(12) United States Patent
Janzen et al.

(10) Patent No.: US 8,409,844 B2
(45) Date of Patent: Apr. 2, 2013

(54) LACTIC ACID BACTERIA PROVIDING IMPROVED TEXTURE OF FERMENTED DAIRY PRODUCTS

(75) Inventors: Thomas Janzen, Frederiksberg (DK); Niels Bang Siemsen Jensen, Frederiksberg (DK)

(73) Assignee: Chr. Hansen A/S, Horsholm (DK)

( * ) Notice: Subject to any disclaimer, the term of this patent is extended or adjusted under 35 U.S.C. 154(b) by 729 days.

(21) Appl. No.: 12/280,467

(22) PCT Filed: Feb. 20, 2007

(86) PCT No.: PCT/DK2007/050023
§ 371 (c)(1), (2), (4) Date: Oct. 13, 2008

(87) PCT Pub. No.: WO2007/095958
PCT Pub. Date: Aug. 30, 2007

(65) Prior Publication Data
US 2009/0226567 A1    Sep. 10, 2009

(30) Foreign Application Priority Data

Feb. 24, 2006  (EP) .................................... 06110394

(51) Int. Cl.
*C12N 1/20* (2006.01)
(52) U.S. Cl. ..................................... 435/253.4; 435/243
(58) Field of Classification Search .................. None
See application file for complete search history.

(56) References Cited

U.S. PATENT DOCUMENTS 7,615,367 B2 *  11/2009  De Vuyst et al. ........... 435/253.4
2006/0240539 A1  10/2006  Horvath et al.

FOREIGN PATENT DOCUMENTS

| EP | 0750043 A | 12/1996 |
| EP | 0889135 A | 1/1999 |
| EP | 0889136 A | 1/1999 |
| WO | WO 01/16329 A2 | 3/2001 |
| WO | WO 03/102204 A2 | 12/2003 |
| WO | WO 2004/085607 A2 | 10/2004 |

OTHER PUBLICATIONS

Levander et al., Applied and Environmental Microbiology, 2001, vol. 67, No. 6, p. 2734-2738.*
Sophie Foley et al., "A Short Noncoding Viral DNA Element Showing Characteristics of a Replication Origin Confers Bacteriophage Resistance to *Streptococcus thermophilus*", Virology 250, 377-387, (1998).
J. R. Broadbent et al., "Biochemistry, Genetics, and Applications of Exopolysaccharide Production in *Streptococcus thermophilus*: a Review", J. Dairy Sci. 86: 407-423, 2003.
A. N. Hassan et al., "Microstructure and Rheology of Yogurt Made with Cultures Differing Only in Their Ability to Produce Exopolysaccharides", J. Dairy Sci. 86:1632-1638, 2003.
Elisabeth J. Faber et al., "The exopolysaccharides produced by *Streptococcus thermophilus* Rs and Sts have the same repeating unit but differ in viscosity of their milk cultures.", Carbohydrate Research 310, (1998) 269-276.
Amanda Forde et al., "Bacteriophage defence systems in lactic acid bacteria", Antonie van Leeuwenhoek 76: 89-113, 1999.
J. M. Sturino et al., "26 Construction of bacteriophage resistant strains of *Streptococcus thermophilus* by pGh9::ISS1 insertional mutagenesis", Departments of Bacteriology and Food Science, University of Wisconsin-Madison, USA, XP-002163735 *Abstract.

* cited by examiner

*Primary Examiner* — Kade Ariani
(74) *Attorney, Agent, or Firm* — Foley & Lardner LLP

(57) ABSTRACT

A novel *Streptococcus thermophilus* (ST) bacterium that gives improved texture in e.g. a fermented milk dairy product.

1 Claim, 1 Drawing Sheet

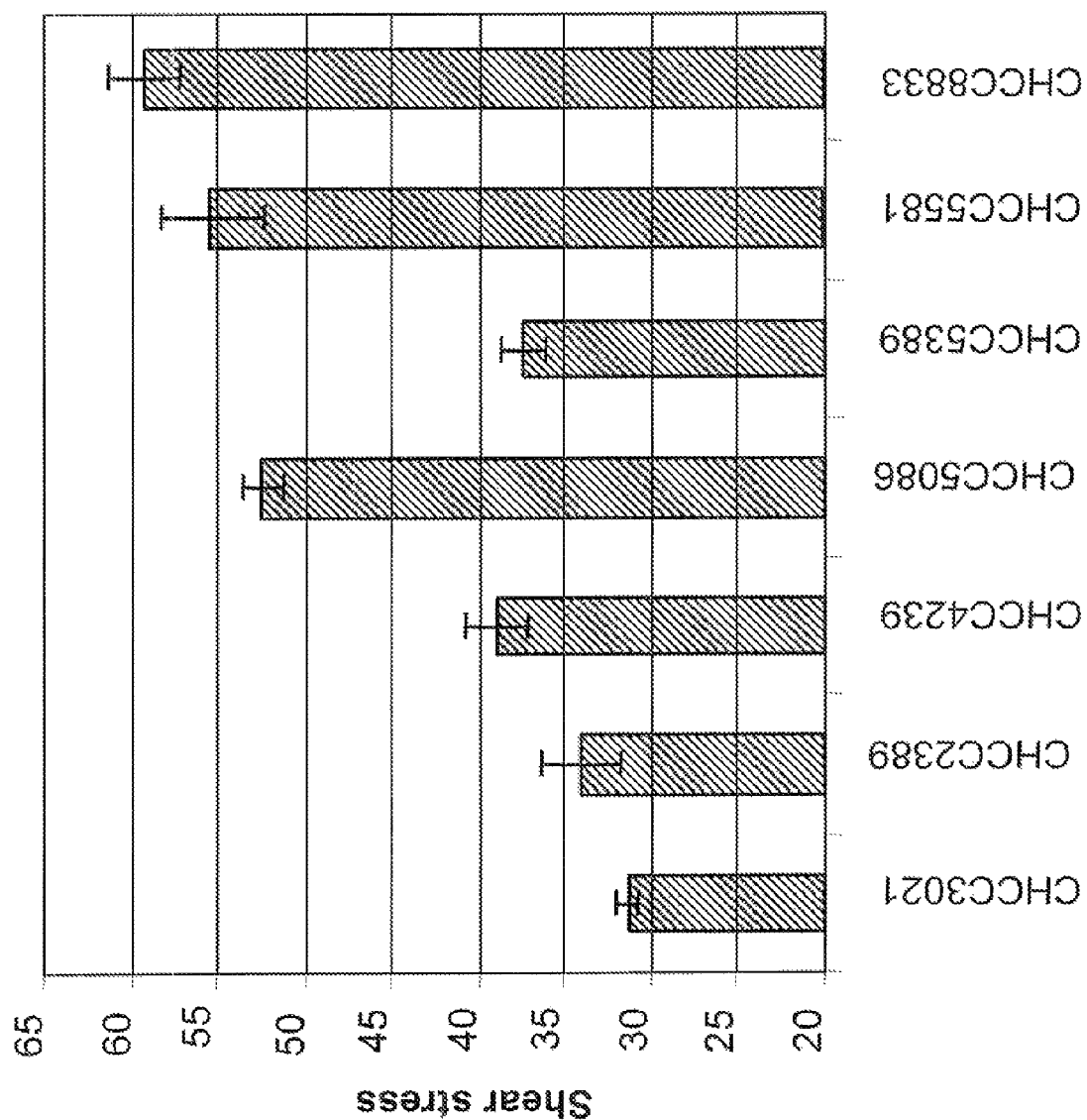

LACTIC ACID BACTERIA PROVIDING IMPROVED TEXTURE OF FERMENTED DAIRY PRODUCTS

FIELD OF THE INVENTION

The present invention relates to a novel *Streptococcus thermophilus* (ST) bacterium that gives improved texture in e.g. a fermented milk dairy product.

BACKGROUND ART

Many strains of *Streptococcus thermophilus* synthesize extracellular polysaccharides (EPS). These molecules may be produced as capsules that are tightly associated with the cell, or they may be liberated into the medium as a loose slime (i.e., "ropy" polysaccharide). Although the presence of exopolysaccharide does not confer any obvious advantage to growth or survival of *S. thermophilus* in milk, in situ production by this species or other dairy lactic acid bacteria typically imparts a desirable "ropy" or viscous texture to fermented milk products. Work has also shown that exopolysaccharide-producing *S. thermophilus* can enhance the functional properties of Mozzarella cheese. For further details see the review article of Broadbent et al. (J. dairy Sci. 86:407-423).

WO2004/085607A2 (Rhodia Chimie) describes a *Streptococcus thermophilus* (ST) strain comprising some specific concrete genes (termed "eps" genes) involved in the biosynthesis of EPS.

Hassan et al. (2003; J. dairy Sci. 86:1632-1638) describes 2 "Ropy" strains of *Streptococcus thermophilus*, CHCC3534 and CHCC3541. Both of these strains are sensitive to phages.

SUMMARY OF THE INVENTION

The problem to be solved by the present invention is to provide a novel *Streptococcus thermophilus* strain with improved properties in particular in relation to being able to give improved texture of fermented dairy products such as e.g. yoghurt and which is useful in present-day highly industrialized dairy production where phage attacks are problematic.

As can be seen in working examples below the herein described novel *Streptococcus thermophilus* (ST) strain with the registration number DSM 178767 (herein also termed CHCC8833), deposited with DSMZ-Deutsche Sammlung von Mikroorganismen and Zellkulturen GmbH at Mascheroder Weg 1b, D-38124 Braunschweig on Jan. 11, 2006, gives improved texture (measured as shear stress) as compared to relevant commercially available ST strains considered as high texturing strains and currently used in the dairy industry. The herein described novel DSM 17876 ST strain does not comprise the specific concrete eps genes described in WO2004/085607A2 (Rhodia Chimie) (determined by a PCR analysis—data not shown). Furthermore, as illustrated in example 2, *Streptococcus thermophilus* strain CHCC8833 has the advantage to be resistant to a large number of phages which occur in dairies.

Accordingly, a first aspect of the invention relates to a lactic acid *Streptococcus thermophilus* (ST) bacterium with the registration number DSM 17876 or a mutant thereof, wherein the mutant strain is obtained by using the deposited strain as starting material, and wherein the mutant has retained or further improved the texturing properties of DSM 17876.

A second aspect of the invention relates to a starter culture composition comprising the bacterium of the first aspect.

A third aspect of the invention relates to a method of manufacturing a food or feed product comprising adding a starter culture composition according to the second aspect to a food or feed product starting material and keeping the thus inoculated starting material under conditions where the bacterium is metabolically active.

Embodiment of the present invention is described below, by way of examples only.

DRAWINGS

FIG. 1: Result showing improved texture (Shear stress) of milk fermented with the novel ST strain compared to commercially available ST strains considered as high texturing strains. The strains are described in example 2. Texture is quantified by assessing the Shear stress measured in Pascals [Pa] by use of a rheometer as described in example 1. Bar indicates 1×S.E.

DETAILED DESCRIPTION OF THE INVENTION

Novel *Streptococcus thermophilus* Strain

A sample of the novel *Streptococcus thermophilus* (ST) strain CHCC8833 has been deposited at DSMZ (Deutsche Sammiung von Mikroorganismen und Zellkulturen GmbH) under the accession number DSM 17876 with a deposit date of 11 Jan. 2006. The deposit has been made under the conditions of the Budapest Treaty on the International Recognition of the Deposit of Microorganisms for the Purposes of Patent Procedure.

The first aspect of the invention relates to the herein described novel strain or "a mutant thereof".

It is clear for the skilled person that by using the deposited strain as starting material, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as starting material.

Since the milk and the conditions in dairies are generally not sterile, bacteriophages constitute a serious threat in the production of dairy products. The phages infect the lactic acid bacteria and propagate in an explosive manner, leading to cell death and as a consequence a defective acidification and failure of the production. Especially in modern dairy industries which apply very large sized vats, phage attacks are associated with very significant monetary losses. Consequently industry constantly strives to develop new phage resistant cultures. As illustrated in example 1 and 2 *Streptococcus thermophilus* strain CHCC8833 (DSM 17876) does not only provide a surprisingly high texture but unexpectedly CHCC8833 was in contrast to other high texturing strains resistant to all phages tested.

A Starter Culture Comprising a LAB as Described Herein

The lactic acid bacterium (LAB) as described herein is useful as starter culture in the production of food or feed products.

Typically, such a starter culture composition comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g.

The composition may as further components contain cryoprotectants and/or conventional additives including nutrients such as yeast extracts, sugars and vitamins.

As it is normal in the production of lactic acid bacterial fermentation processes to apply mixed cultures of lactic acid bacteria, the composition will in certain embodiments comprise a multiplicity of strains either belonging to the same species or belonging to different species. A typical example of such a useful combination of lactic acid bacteria in a starter culture composition is a mixture of a *Leuconostoc* sp. and one or more *Lactococcus* subsp. such as *Lactococcus lactis* subsp. *lactis, Lactococcus lactis* subsp. *cremods* or *Lactococcus lactis* subsp. *lactis biovar. diacetylactis.*

A Method of Manufacturing a Food or Feed Product

As said above, an aspect of the invention relates to a method of manufacturing a food or feed product comprising adding a starter culture composition as described herein to a food or feed product starting material and keeping the thus inoculated starting material under conditions where the lactic acid bacterium is metabolically active.

Useful food product starting materials include any material which is conventionally subjected to a lactic acid bacterial fermentation step such as milk, vegetable materials, meat products, fruit juices, must, doughs and batters.

The fermented products, which are obtained by the method, include as typical examples dairy products such as fermented milk, yoghurt, cheese including fresh cheese products or mozzarella, and buttermilk.

For further examples and details of herein relevant fermented food products reference is made to the review article of Broadbent et al (J. dairy Sci. 86:407-423), where relevant fermented food products are described in the sections with title "Application in Yoghurt and Fermented Milks" and "Application in Mozzarella Cheese".

In further embodiments, the substrate material is a starting material for an animal feed such as silage, e.g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

EXAMPLES

Example 1

CHCC8833—Elevated Texture in a Fermented Milk

Strains:
CHCC8833: Novel DSM 17876 ST strain as described herein.
 Reference strains: see example 2.
 All strains are commercial strains generally considered to be high texturing strains.
Fermentation of Milk
 Frozen concentrate of the ST strains were used to inoculate 200 mL reconstituted milk with a dry matter content of 9.5%, which had been heat treated to 99° C. for 15 minutes in a batch process. Frozen concentrates of CHCC8833 typically display a cell count between $1·10^9$ and $1·10^{10}$ cfu/g. The rate of inoculation was 1 g concentrate per 10 L milk, hence between $1·10^5$ and $1·10^6$ cfu/mL milk. The incubation took place at 37° C. until pH reached 4.55, at which time the coagulation of the milk had taken place. The fermented milk was then cooled to 5° C.

Analysis of Texture in a Fermented Milk
 The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system.
 The viscometry test was made with shear rates varying from 0.27 to 300 s$^{-1}$ in 21 steps. Shear rates were increased and then decreased and the upward and downward curves of shear stress (Pascal, Pa.) and apparent viscosity (Pa*s) were recorded. Delay and integration times were 5 s and 10 s, respectively. For further analysis, shear stress at 300 s$^{-1}$ was chosen.
Results and Conclusions
 Fermented milks incubated with concentrates of *Streptococcus thermophilus* strains that are currently used in the dairy industry (reference strains) showed to be less viscous (smaller shear stress) compared to samples produced with CHCC8833 (see FIG. 1 herein).

Example 2

CHCC8833—Phage Resistance Profile

Bacterial Strains:
CHCC2389: *Streptococcus thermophilus* strain ST143, commercially available from Chr. Hansen A/S as F-DVS ST143, material no.: 200144. CHCC2389 and CHCC3534 (Hassan et al. 2003) are different isolates of the same strain.
CHCC3021: *Streptococcus thermophilus* strain ST10255, commercially available from Chr. Hansen A/S as F-DVS ST-BODY-2, material no.: 623155.
CHCC3541: *Streptococcus thermophilus* strain ST20, commercially available from Chr. Hansen A/S as F-DVS ST20X, material no.: 501696.
CHCC4239: *Streptococcus thermophilus* strain ST4239, commercially available from Chr. Hansen A/S in mixed culture F-DVS ABY-4, material no.: 675175.
CHCC5086: *Streptococcus thermophilus* strain 5086, commercially available from Chr. Hansen A/S in mixed culture F-DVS YF-LX701, material no.: 660656.
CHCC5389: *Streptococcus thermophilus* strain 5389, commercially available from Chr. Hansen A/S in mixed culture F-DVS ABY-4, material no.: 675175
CHCC5581: *Streptococcus thermophilus* strain TA40, commercially available from Danisco A/S
CHCC8833: *Streptococcus thermophilus* strain DSM 17876.
Phage Testing
 The phage sensitivity of the above mentioned high texturing commercial strains were compared by spot testing with a test-panel of phages comprising 43 separate phage isolates.
 The spot test is an agar overlay method to enumerate the number of bacteriophages in a sample. The method involves the plating of the bacterial strain to be tested with the help of a soft top agar on the surface of an agar plate (bottom agar). Different dilutions of the cell free phage isolates are then spotted on the top agar. Single phages will attack a bacterial cell and replicate releasing phage particles to attack and lyse bacteria in their proximity, resulting in clear areas (plaques) surrounded by opaque culture growth, see Adams, M. H. (1959). Bacteriophages. Interscience Publishers, Inc., New York.

Method

Briefly, 10 ul of a phage lysate (Plaque forming units (PFU) approx. $10^9$/ml) were spotted undiluted and in 1:100 dilution on the bacterial strain to be tested (host strain) and incubated at 37° C. over night.

The agar used was M17 agar (Oxoid CM785)+2% lactose, essentially prepared as recommended by the supplier (Oxoid Ltd., Basingstoke, Hampshire, UK).

A clear zone at 1:100 dilution or single plaques were considered to be caused by a phage attack and be indicative.

Results and Conclusions

The results of the spot testing were that CHCC2389, CHCC3021, CHCC3534, CHCC3541, CHCC4239 and CHCC5086 were found to be sensitive towards phages. CHCC5381 has previously been found to be sensitive to phages. Interestingly, no phages were found to attack CHCC8833.

Deposited Microbial Organisms [EXPERT SOLUTION]

Regarding Rule 13bis.6 (PCT), applicant requests "expert solution" for samples of the microbial organism mentioned in the present patent in all territories where such a solution may apply.

In particular it is requested, that regarding:

Europe

In respect to those designations in which a European Patent is sought a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies. (Rule 28 (4) and 28 (5) EPC).

Canada

The applicant requests that, until either a Canadian patent has been issued on the basis of an application or the application has been refused, or is abandoned and no longer subject to reinstatement, or is withdrawn, the Commissioner of Patents only authorizes the furnishing of a sample of the deposited biological material referred to in the application to an independent expert nominated by the Commissioner, the applicant must, by a written statement, inform the International Bureau accordingly before completion of technical preparations for publication of the international application.

Norway

The applicant hereby requests that, until the application has been laid open to public inspection (by the Norwegian Patent Office), or has been finally decided upon by the Norwegian Patent Office without having been laid open inspection, the furnishing of a sample shall only be effected to an expert in the art. The request to this effect shall be filed by the applicant with the Norwegian Patent Office not later than at the time when the application is made available to the public under Sections 22 and 33(3) of the Norwegian Patents Act. If such a request has been filed by the applicant, any request made by a third party for the furnishing of a sample shall indicate the expert to be used. That expert may be any person entered on the list of recognized experts drawn up by the Norwegian Patent Office or any person approved by the applicant in the individual case.

Australia

The applicant hereby gives notice that the furnishing of a sample of a microorganism shall only be effected prior to the grant of a patent, or prior to the lapsing, refusal or withdrawal of the application, to a person who is a skilled addressee without an interest in the invention (Regulation 3.25(3) of the Australian Patents Regulations).

Finland

The applicant hereby requests that, until the application has been laid open to public inspection (by the National Board of Patents and Regulations), or has been finally decided upon by the National Board of Patents and Registration without having been laid open to public inspection, the furnishing of a sample shall only be effected to an expert in the art.

United Kingdom

The applicant hereby requests that the furnishing of a sample of a microorganism shall only be made available to an expert. The request to this effect must be filed by the applicant with the International Bureau before the completion of the technical preparations for the international publication of the application.

Denmark

The applicant hereby requests that, until the application has been laid open to public inspection (by the Danish Patent Office), or has been finally decided upon by the Danish Patent office without having been laid open to public inspection, the furnishing of a sample shall only be effected to an expert in the art. The request to this effect shall be filed by the applicant with the Danish Patent Office not later that at the time when the application is made available to the public under Sections 22 and 33(3) of the Danish Patents Act. If such a request has been filed by the applicant, any request made by a third party for the furnishing of a sample shall indicate the expert to be used. That expert may be any person entered on a list of recognized experts drawn up by the Danish Patent Office or any person by the applicant in the individual case.

Sweden

The applicant hereby requests that, until the application has been laid open to public inspection (by the Swedish Patent Office), or has been finally decided upon by the Swedish Patent Office without having been laid open to public inspection, the furnishing of a sample shall only be effected to an expert in the art. The request to this effect shall be filed by the applicant with the International Bureau before the expiration of 16 months from the priority date (preferably on the Form PCT/RO/134 reproduced in annex Z of Volume I of the PCT Applicant's Guide). If such a request has been filed by the applicant any request made by a third party for the furnishing of a sample shall indicate the expert to be used. That expert may be any person entered on a list of recognized experts drawn up by the Swedish Patent Office or any person approved by a applicant in the individual case.

Netherlands

The applicant hereby requests that until the date of a grant of a Netherlands patent or until the date on which the application is refused or withdrawn or lapsed, the microorganism shall be made available as provided in the 3 IF(1) of the Patent Rules only by the issue of a sample to an expert. The request to this effect must be furnished by the applicant with the Netherlands Industrial Property Office before the date on which the application is made available to the public under Section 22C or Section 25 of the Patents Act of the Kingdom of the Netherlands, whichever of the two dates occurs earlier.

Iceland

The applicant hereby requests that until a patent has been granted or a final decision taken by the Icelandic Patent Office concerning an application which has not resulted in request to this effect shall be filed by the applicant with the Icelandic Patent Office not later than at a time when the application is made available to the public under Sections 22 and 33(3) of the Icelandic Patent Act. If such a request has been filed by the applicant, any request made by a third party for the furnishing of a sample shall indicate the expert to be used. That expert may be any person entered on a list of recognized experts drawn up by the Icelandic Patent Office or any person by the applicant in the individual case.

Singapore

The applicant hereby requests that the furnishing of a sample of a microorganism shall only be made available to an expert.

Slovenia

The applicant hereby requests that the furnishing of samples to a third party is subject to the condition that that party: (a) has the right to demand that a sample of the microorganism be made available; (b) has undertaken to ensure that the applicant does not authorize access to the sample of the deposited microorganism to any third party before the expiry of the prescribed period of validity of the patent.

Switzerland

The applicant hereby requests that the furnishing of samples to a third party is subject to the conditions that that party indicates to the depository institution its! name and address for the purpose of information of the depositor and undertakes: (a) not to make available the deposited culture or a culture derived from it to a third party; (b) not to use the culture outside the purview of the law; (c) to produce, in case of a dispute, evidence that the obligations under items (a) and (b) have not been violated.

The Former Yugoslav Republic of Macedonia

The applicant hereby requests that the furnishing of samples to a third party is subject to the condition that that party: (a) has the right to demand that a sample of the microorganism be made available; (b) has undertaken to ensure that the applicant does not authorize access to the sample of the deposited microorganism to any third party before the expiry of the prescribed period of validity of the patent.

The invention claimed is:

1. An isolated strain of lactic acid bacterium *Streptococcus thermophiles* (ST) deposited under the accession number D5M 17876 or a mutant strain thereof, wherein the mutant strain is obtained from the deposited strain as starting material, and wherein the mutant has the same texturizing properties as parent strain DSM 17876, or has improved texturizing properties compared to said parent strain DSM 17876.

* * * * *

UNITED STATES PATENT AND TRADEMARK OFFICE
CERTIFICATE OF CORRECTION

PATENT NO. : 8,409,844 B2  Page 1 of 1
APPLICATION NO. : 12/280467
DATED : April 2, 2013
INVENTOR(S) : Janzen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Signed and Sealed this

First Day of September, 2015

Michelle K. Lee
*Director of the United States Patent and Trademark Office*